US012721607B1

(12) United States Patent
Yusuf et al.

(10) Patent No.: US 12,721,607 B1
(45) **Date of Patent: *Sep. 1, 2026**

(54) COLLAPSIBLE FLUID COLLECTION SYSTEM FOR POINT-OF-CARE DIAGNOSTICS

(71) Applicant: George Mason University, Fairfax, VA (US)

(72) Inventors: Sameen Yusuf, Fairfax, VA (US); Marissa A. Howard, Fairfax, VA (US); Sara Sharif, Fairfax, VA (US); Kelsey Mitchell, Fairfax, VA (US); Amanda Haymond Still, Fairfax, VA (US); Ngoc Bao Vuong, Fairfax, VA (US); Alessandra Luchini Kunkel, Fairfax, VA (US); Lance A. Liotta, Fairfax, VA (US)

(73) Assignee: George Mason University, Fairfax, VA (US)

( * ) Notice: Subject to any disclaimer, the term of this patent is extended or adjusted under 35 U.S.C. 154(b) by 98 days.

This patent is subject to a terminal disclaimer.

(21) Appl. No.: 18/537,539

(22) Filed: Dec. 12, 2023

Related U.S. Application Data

(63) Continuation of application No. 16/391,942, filed on Apr. 23, 2019, now Pat. No. 11,857,169.

(Continued)

(51) Int. Cl.

| | |
|---|---|
| ***A61B 10/00*** | (2006.01) |
| ***A61B 5/15*** | (2006.01) |

(52) U.S. Cl.

CPC ...... *A61B 10/007* (2013.01); *A61B 5/150755* (2013.01); *A61B 10/0051* (2013.01); *A61B 5/150343* (2013.01)

(58) Field of Classification Search

CPC ........... A61B 10/007; A61B 5/150755; A61B 10/0051; A61B 5/150343; A61B 10/0045;

(Continued)

(56) References Cited

U.S. PATENT DOCUMENTS

| | | | |
|---|---|---|---|
| 4,494,581 | A | 1/1985 | Gordon |
| 4,751,751 | A | 6/1988 | Reno |

(Continued)

*Primary Examiner* — Benjamin S Melhus

(74) *Attorney, Agent, or Firm* — Bradley Arant Boult Cummings LLP; Daniel E. Sineway, Esq.; Anna Baker, Esq.

(57) ABSTRACT

A collapsible sample collection device with a novel, collapsible 3D capture open affinity net dispersed throughout the volume of the container, said net with tethered affinity moieties, is designed to address the need for low-cost, simple harvesting and concentration of diagnostic analytes that generally does not require any ancillary equipment. The collection device generally permits analytes of interest to be efficiently harvested from body fluid samples, concentrated, collapsed into a flat mailing size, and protected from degradation without the need for traditional cold chain technologies. The concentration factor will increase sensitivity by several orders of magnitude when coupled with any type of downstream analyte measurement, including point of care testing. The collection device, in various embodiments, obviates the need for handling transport or storage of the fluid portion of the body fluid sample (e.g. blood, urine, saliva, etc.) with a volumetric concentration factor of 5 to 100 fold.

20 Claims, 3 Drawing Sheets

Related U.S. Application Data

(60) Provisional application No. 62/661,193, filed on Apr. 23, 2018.

(58) Field of Classification Search
CPC ........ A61B 10/0096; A61B 2010/0006; A61B 2010/0074; A61B 5/20; A61B 2010/0003; A61B 10/0038; A61B 2010/0009; A61B 2010/0077; A61B 5/00; A61B 5/14507; A61B 10/0012; A61B 10/0064; A61B 10/02; A61B 2010/0061; A61B 2010/0216; A61B 2017/0046; A61B 2018/0212; A61B 2090/037; A61B 2560/04; A61B 2560/0406; A61B 5/145; A61B 5/207; A61B 5/4337; A61B 5/7405; A61B 90/50; A61F 5/4556; A61F 5/453; A61F 2005/4402; A61F 5/4404; A61F 5/455; B01L 3/502; B01L 2300/0825; B01L 2300/0832; B01L 3/5023; B01L 3/5029; B01L 2200/0621; B01L 2300/0663; B01L 2300/069; B01L 2400/0406; B01L 2400/0478; B01L 2400/0644; B01L 3/5027; B01L 2200/027; B01L 2200/0605; B01L 2200/0631; B01L 2200/0689; B01L 2300/0609; B01L 2300/0672; B01L 2300/0681; B01L 2300/0861; B01L 2300/0864; B01L 2300/123; B01L 2400/0633; B01L 3/5021; B01L 3/505; B01L 9/06; B01L 2200/026; B01L 2200/04; B01L 2200/087; B01L 2200/143; B01L 2200/16; B01L 2300/042; B01L 2300/043; B01L 2300/047; B01L 2300/06; B01L 2300/0851; B01L 2300/126; B01L 2400/0433; B01L 2400/0683; B01L 3/00; B01L 3/502715; B01L 3/502761; B01L 3/5055; B01L 3/508; B01L 3/5082; B01L 3/50825; B01L 3/523; B01L 3/5635; G01N 1/18; G01N 21/78; G01N 33/48714; G01N 33/54366; G01N 1/4005; G01N 1/405; G01N 1/4077; G01N 2001/028; G01N 2001/4088; G01N 2021/7759; G01N 2021/7793; G01N 33/48757; G01N 33/48778; G01N 33/493; G01N 33/521; G01N 33/54387; G01N 33/548; G01N 33/76
See application file for complete search history.

(56) References Cited

U.S. PATENT DOCUMENTS

| | | | | |
|---|---|---|---|---|
| 5,368,583 | A | 11/1994 | Fleury | |
| 5,408,703 | A | 4/1995 | Cicio | |
| 5,427,739 | A | 6/1995 | Meserol | |
| 5,605,161 | A | 2/1997 | Cross | |
| 6,460,200 | B1 | 10/2002 | Mottale | |
| 6,493,884 | B1 | 12/2002 | Muller | |
| 9,931,103 | B1 | 4/2018 | DeLaRosa | |
| 2003/0185708 | A1 | 10/2003 | Otake | |
| 2004/0184954 | A1 | 9/2004 | Guo | |
| 2005/0119589 | A1 | 6/2005 | Tung | |
| 2005/0202568 | A1 | 9/2005 | Tung | |
| 2008/0183102 | A1* | 7/2008 | Dunkin | A61B 10/007 600/580 |
| 2010/0174209 | A1 | 7/2010 | Fleshman | |
| 2010/0256349 | A1 | 10/2010 | Ruhstorfer et al. | |
| 2010/0263113 | A1 | 10/2010 | Shelton et al. | |
| 2011/0190663 | A1 | 8/2011 | Manz | |
| 2014/0276214 | A1 | 9/2014 | Lipinsky | |
| 2014/0276216 | A1 | 9/2014 | Lipinsky | |
| 2015/0223783 | A1 | 8/2015 | Eschete | |
| 2015/0250456 | A1 | 9/2015 | Olgun | |
| 2016/0123856 | A1 | 5/2016 | Slowey | |
| 2016/0327553 | A1 | 11/2016 | Edwards | |
| 2017/0105707 | A1 | 4/2017 | Senior | |
| 2017/0333245 | A1 | 11/2017 | Shi | |
| 2018/0153479 | A1 | 6/2018 | Hu | |
| 2018/0303465 | A1* | 10/2018 | Lyon | A61B 10/007 |
| 2019/0015082 | A1 | 1/2019 | Little | |
| 2019/0125316 | A1 | 5/2019 | Tariyal | |
| 2019/0223842 | A1 | 7/2019 | Hedegaard | |
| 2019/0250075 | A1 | 8/2019 | Wu | |
| 2020/0367864 | A1 | 11/2020 | Bajaj | |
| 2021/0396628 | A1 | 12/2021 | Wu | |

* cited by examiner 300
304
306
302

300
100
302
104

COLLAPSIBLE FLUID COLLECTION SYSTEM FOR POINT-OF-CARE DIAGNOSTICS

CROSS REFERENCE TO RELATED APPLICATIONS

This application is a continuation application and claims priority to, the benefit of, and incorporates by reference herein in its entirety U.S. Non-Provisional application Ser. No. 16/391,942, filed Apr. 23, 2019, entitled "Collapsible Fluid Collection System for Point-of-Care Diagnostics," and U.S. Provisional Patent Application No. 62/661,193, filed Apr. 23, 2018, and entitled "Collapsible Fluid Collection System for Point-of-Care Diagnostics."

STATEMENT REGARDING FEDERALLY-SPONSORED RESEARCH

This invention was made with government support under grant CA206937 awarded by the National Institutes of Health. The government has certain rights in the invention.

TECHNICAL FIELD

The present disclosure relates generally to medical diagnostic tests and, more particularly, to collapsible sample collection kits for body fluid diagnostic tests.

BACKGROUND

Delays in diagnosis generally lead to delayed treatment, thereby exacerbating the condition and further spreading the disease. For the sake of controlling and managing disease epidemics, particularly those of communicable diseases (e.g., Ebola, HIV, gonorrhea, chlamydia, etc.), early diagnosis reduces morbidity and mortality rates. Current diagnostics on the market, however, fail to provide sensitive results in a cost-effective and timely manner. To truly fight off communicable diseases and meet major sustainable development goals of achieving a tuberculosis-, malaria-, and HIV-free world, there is a need to more rapidly and accurately identify and treat the unknown cases of communicable (and other) diseases.

Patient procrastination and hesitation towards seeking medical treatment, known as patient delay, occurs for a variety of socioeconomic reasons. Patients often delay seeking medical advice (up to 120 days after their first onset of symptoms) due to the stigma related their potential diagnosis, the far distance of healthcare centers, and the cost of serial treatment visits. Most diagnostic methods require patients to visit a healthcare facility and have complex, invasive, and expensive tests performed, but the current healthcare infrastructure is highly centralized at hospitals and clinics, contributing to the long distances and overall patient delay.

Unfortunately, disease biomarkers demonstrate low concentrations within urine, and current urinary assays are neither sensitive nor rapid enough to be effective. Present day urinary analysis generally involves storage and shipping of large volumes in uncontrolled environments for prolonged periods of time. Analysis of the urine sample usually must occur in a laboratory site where an experienced technician utilizes advanced machinery typically unavailable to resource-poor settings and everyday individuals. Additionally, other bodily fluid samples, such as blood, fail to concentrate the analyte of interest and preserve against degradation.

Therefore, there is a long-felt but unresolved need for rapid diagnostics and simple sample collection kits that are noninvasive and only require a small sample of a bodily fluid, such as urine, to be effective.

BRIEF SUMMARY OF THE DISCLOSURE

Briefly described, and according to one embodiment, aspects of the present disclosure generally relate to rapid diagnostics and simple sample collection kits that are non-invasive and only require a small sample of a bodily fluid, such as urine, to be effective.

In various embodiments, the collection kit/device comprises a dry fluid collection vessel containing a collapsible, 3-D, open, continuous net of tethered affinity capture moieties (also referred to herein as an "affinity net"), useful for separating analytes from a fluid sample. The affinity net, when inserted into a collection vessel, generally fills the 3-D volume of the dry fluid collection vessel (e.g., a collection vessel volume of one to 100 mL), yet may occupy only approximately one percent of the total volume of the container. The collection kit generally eliminates the requirement to handle, mail, ship, or refrigerate the fluid volume portion containing a diagnostic analyte in any type of body fluid sample (e.g., blood, urine, saliva, etc.). In one embodiment, the dry fluid collection vessel comprises a collapsible collection container, made from a water-resistant and foldable material, that can be used at home or in a clinic to separate a desired analyte from the urine in one step by pouring out the fluid sample and collapsing the container flat. The collapsed container generally retains, in the affinity net, substantially all of the analytes distributed throughout the full volume of the fluid and may be simply mailed in a standard envelope to a lab, doctors-office, or clinic for analysis. Alternatively, the analyte(s) retained in the collapsed container, in one embodiment, may be eluted for measurement on site by a point of care assay device. The elution buffer may be contained within the collapsible device or in a lid, in various embodiments, such that when the emptied container is collapsed, the elution buffer will be discharged to re-wet and elute the analytes from the collapsed affinity capture net.

The affinity net, in various embodiments, does not absorb fluids and has no significant wicking, imbibing, or capillary fluid retention properties, which generally distinguishes the material from a bibulous paper or other porous material that, in contrast, retain and hold a fluid sample. The lack of bibulous properties of the affinity net generally permits the complete collapse of the affinity net material so that the total content of the analytes in the entire fluid volume may be collapsed into a volume that is less than the original fluid volume (e.g., 1%, 5%, 10%, 25%, etc.). In another embodiment, the affinity net comprises a high affinity moiety, such as a dye, organic dye, ligand, nucleic acid, protein, antibodies, aptamers, enzyme substrates, metal, drug, affinity tag recognizing material, etc., that is tethered to the net material. The affinity moiety generally captures the analyte, preserves the analyte, and pulls it out of solution phase. In yet another embodiment, the high affinity moiety is shielded within an open porous material (e.g., hydrogel, etc.), which generally prevents direct strand to strand adherence or obstruction of access to the dye, thereby permitting rapid free exchange of the analyte from the fluid to the solid state of the affinity moiety. The shielding may also be employed to exclude unwanted molecules. In a particular embodiment, Nanotraps® particles from Ceres Nanosciences are packaged into porous colloidal hydrogel particles that float buoyant in solution for optimal exchange with the solvent.

In one specific embodiment, the affinity net comprises spun glass silica polymer strands of a diameter less than 10 microns (e.g., 8, 5, 2.5, etc.). The surface of the continuous silica strands generally is studded with affinity molecule containing hydrogel particles generally less than 1 micron in size or coated with an approximately 500-nM layer of porous hydrogel containing affinity dye molecules. The porosity of the hydrogel, in one embodiment, permits rapid exchange of the analytes of interest into the hydrogel where the analytes are captured by the affinity moiety. In another embodiment, the affinity moiety is a dye that binds the analyte with high on rate or low off rate, thereby rapidly sequestering the analyte out of solution so that the analyte becomes tethered to the net. In yet another embodiment, the affinity net comprises fixed distributed affinity particles with a central core containing an affinity ligand and a porous shell that permits entry of the analyte.

The collection device, in various embodiments, may be used to gather any analyte suspended or dissolved in any fluid. In one non-limiting example, for one type of body fluid testing, the collection kit is used for urine collection from a subject. The subject generally uses the collection kit by: 1) urinating into the collection vessel; 2) dumping out and discarding the urine fluid from the container leaving the captured analyte tethered to the net; and 3) at this instance, either collapsing the container and placing the container into a mailing envelop for delivery to the lab or puncturing/releasing a solution to liberate the analyte of interest from the affinity net, wherein the remaining solution contains the analyte of interest and may be applied to any immunological diagnostic tool.

Generally, the collection device improves body fluid diagnostics in the field, at home, in school, in rural settings, or in clinics. In various embodiments, the concentration factor afforded by the collection device may comprise 100×-1,000×, or more, thereby dramatically enhancing the analytical sensitivity of body fluid diagnostic tests; the preservation of the analyte in a solid state out of solution obviates the need for freezing or transport of hazardous liquid body fluid, thereby improving the ease of use and cost of body fluid diagnostic tests.

In one embodiment, a collapsible collection container, comprising: a vessel comprising a nonabsorbent material that is capable of being collapsed or folded from a generally-conical shape into a substantially-flat shape, wherein the vessel defines an opening for accepting a fluid; and an affinity net that rests within the vessel.

In one embodiment, a method of using a collapsible collection container, comprising the steps of: expanding a vessel comprising a nonabsorbent material from a substantially-flat shape into a generally-conical or tapered shape, wherein the vessel defines an opening for accepting a fluid, and an affinity net that rests within the vessel; introducing a fluid into the vessel through the opening such that the affinity net comes into contact with the fluid for a predetermined amount of time; after the predetermined amount of time, draining the fluid from the vessel; and collapsing the vessel from the generically-conical shape back into the substantially-flat shape, wherein the affinity net is still within the vessel.

In one embodiment, a method of manufacturing an affinity net, comprising the steps of: acid treating glass wool; drying the acid-treated glass wool; incubating the dried treated glass wool with nanoparticles; and drying the incubated glass wool.

In one embodiment, a kit for collecting bodily fluids, comprising: a vessel comprising a nonabsorbent material that is capable of being collapsed or folded from a generically-conical shape into a substantially-flat shape, wherein the vessel defines an opening for accepting a bodily fluid and an affinity net that rests within the vessel; an envelope for holding the collapsed vessel before and after introduction of the bodily fluid; and instructions for using the vessel to collect the bodily fluid.

According to one aspect of the present disclosure, the container, wherein the vessel further defines a body for retaining the fluid and wherein the affinity net rests within the body. Furthermore, the container, wherein the body further defines a second opening such that the fluid flows through the body, coming into contact with the affinity net therein, and out the second opening. Moreover, the container, wherein the nonabsorbent material comprises a plastic, laminated plastic, laminated paper, or laminated cardboard. Additionally, the container further comprising a viewing window and a fill indicator. Further, the container, wherein the affinity net comprises a high affinity moiety that has been tethered to a non-bibulous material to capture a particular analyte. Also, the container, wherein the high affinity moiety comprises a dye, ligand, nucleic acid, protein, antibody, aptamer, enzyme substrate, metal, drug, or affinity tag recognizing material. In addition, the container, wherein the non-bibulous material comprises glass wool, cellulose fibers, activated nitrocellulose fibers, or polymer. As well, the container, wherein the particular analyte is indicative of tuberculosis, Chagas disease, tick-borne diseases, pregnancy, communicable/infectious diseases, malaria, human growth hormone, cancer, or cardiac disease. Furthermore, the container, wherein the fluid comprises urine, saliva, or blood.

According to one aspect of the present disclosure, the method, wherein the fluid comprises urine, saliva, or blood. Moreover, the method, wherein the nonabsorbent material comprises a plastic, laminated plastic, laminated paper, or laminated cardboard. Additionally, the method, wherein the vessel further comprises a viewing window and a fill indicator to ensure that the proper amount of fluid is introduced into the vessel. Further, the method, wherein the affinity net comprises a high affinity moiety that has been tethered to a non-bibulous material to capture a particular analyte. Also, the method, wherein the high affinity moiety comprises a dye, ligand, nucleic acid, protein, antibody, aptamer, enzyme substrate, metal, drug, or affinity tag recognizing material and the non-bibulous material comprises glass wool, cellulose fibers, activated nitrocellulose fibers, or polymer. In addition, the method, wherein the particular analyte is indicative of tuberculosis, Chagas disease, tick-borne diseases, pregnancy, communicable/infectious diseases, malaria, human growth hormone, cancer, or cardiac disease. As well, the method, further comprising the steps of placing the collapsed vessel into an envelope for transport to a laboratory for further analysis and causing the envelope to be transported to the laboratory. Furthermore, the method, further comprising the steps of extracting the particular analyte from the affinity net and determining whether a test subject has tuberculosis, Chagas disease, tick-borne diseases, pregnancy, communicable/infectious diseases, malaria, human growth hormone, cancer, or cardiac disease. Moreover, the method, further comprising the step of compressing the affinity net to concentrate the affinity net into a reduced volume in the collection device using a diagnostic tool, wherein the diagnostic tool comprises an immunoassay or other analytical measure system.

Additionally, the method, wherein the step of incubating occurs for at least one hour. Further, the method, wherein the step of drying the incubated glass wool occurs for at least 15 minutes in an oven and wherein the temperature of the oven is 85° C. Also, the method, further comprising the steps of: washing the dried incubated glass wool to remove excess nanoparticles; cutting the washed glass wool into particular lengths and/or weights; and freeze drying the cut glass wool. In addition, the method, wherein the nanoparticles comprise Reactive Blue 221 dyed nanoparticles.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
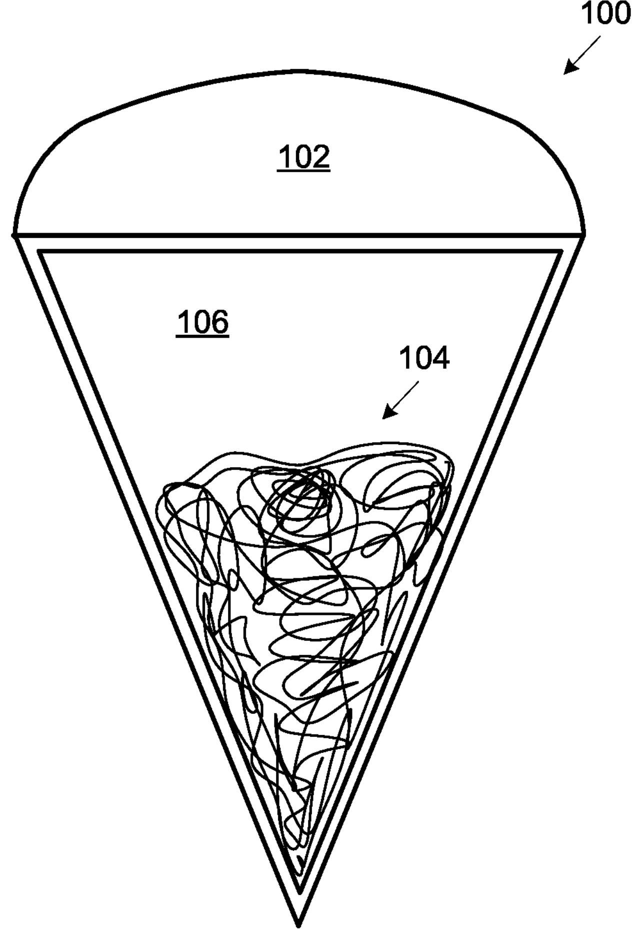
FIG. 1 illustrates an exemplary collapsible container/kit, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. As will be understood and appreciated, the accompanying drawings represent merely one approach or embodiment of the present disclosure, and other aspects are used according to various embodiments of the present disclosure. As will be understood by one having ordinary skill in the art, the steps and processes disclosed herein may operate concurrently and continuously, are generally asynchronous and independent, and are not necessarily performed in the order disclosed. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to rapid diagnostics and simple sample collection kits that are non-invasive and only require a small sample of a bodily fluid, such as urine, to be effective.

In various embodiments, the collection kit/device comprises a dry fluid collection vessel containing a collapsible, 3-D, open, continuous net of tethered affinity capture moieties (also referred to herein as an "affinity net"), useful for separating analytes from a fluid sample. The affinity net, when inserted into a collection vessel, generally fills the 3-D volume of the dry fluid collection vessel (e.g., a collection vessel volume of one to 100 mL), yet may occupy only approximately one percent of the total volume of the container. The collection kit generally eliminates the requirement to handle, mail, ship, or refrigerate the fluid volume portion containing a diagnostic analyte in any type of body fluid sample (e.g., blood, urine, saliva, etc.). In one embodiment, the dry fluid collection vessel comprises a collapsible collection container, made from a water-resistant and foldable material, that can be used at home or in a clinic to separate a desired analyte from the urine in one step by pouring out the fluid sample and collapsing the container flat. The collapsed container generally retains, in the affinity net, substantially all of the analytes distributed throughout the full volume of the fluid and may be simply mailed in a standard envelope to a lab, doctors-office, or clinic for analysis. Alternatively, the analyte(s) retained in the collapsed container, in one embodiment, may be eluted for measurement on site by a point of care assay device. The elution buffer may be contained within the collapsible device or in a lid, in various embodiments, such that when the emptied container is collapsed, the elution buffer will be discharged to re-wet and elute the analytes from the collapsed affinity capture net.

The affinity net, in various embodiments, does not absorb fluids and has no significant wicking, imbibing, or capillary fluid retention properties, which generally distinguishes the material from a bibulous paper or other porous material that, in contrast, retain and hold a fluid sample. The lack of bibulous properties of the affinity net generally permits the complete collapse of the affinity net material so that the total content of the analytes in the entire fluid volume may be collapsed into a volume that is less than the original fluid volume (e.g., 1%, 5%, 10%, 25%, etc.). In another embodiment, the affinity net comprises a high affinity moiety, such as a dye, organic dye, ligand, nucleic acid, protein, antibodies, aptamers, enzyme substrates, metal, drug, affinity tag recognizing material, etc., that is tethered to the net material or integral with the net structure or integral within pores or cavities within the structure of the net strands. The affinity moiety generally captures the analyte, preserves the analyte, and pulls it out of solution phase. In yet another embodiment, the high affinity moiety is shielded within an open porous material (e.g., hydrogel, etc.), which generally prevents direct strand to strand adherence or obstruction of access to the dye, thereby permitting rapid free exchange of the analyte from the fluid to the solid state of the affinity moiety. The shielding may also be employed to exclude unwanted molecules. In a particular embodiment, Nanotraps® particles from Ceres Nanosciences are packaged into porous colloidal hydrogel particles that float buoyant in solution for optimal exchange with the solvent.

In one specific embodiment, the affinity net comprises spun glass silica polymer strands of a diameter less than 10 microns (e.g., 8, 5, 2.5, etc.). The surface of the continuous silica strands generally is studded with affinity molecule containing hydrogel particles generally less than 1 micron in size or coated with an approximately 500-nM layer of porous hydrogel containing affinity dye molecules. The porosity of the hydrogel, in one embodiment, permits rapid exchange of the analytes of interest into the hydrogel where the analytes are captured by the affinity moiety. In another embodiment, the affinity moiety is a dye that binds the analyte with high on rate or low off rate, thereby rapidly sequestering the analyte out of solution so that the analyte becomes tethered to the net. In yet another embodiment, the affinity net comprises fixed distributed affinity particles with a central core containing an affinity ligand and a porous shell that permits entry of the analyte.

The collection device, in various embodiments, may be used to gather any analyte suspended or dissolved in any fluid. In one non-limiting example, for one type of body fluid testing, the collection kit is used for urine collection from a subject. The subject generally uses the collection kit by: 1) urinating into the collection vessel; 2) dumping out and discarding the urine fluid from the container leaving the captured analyte tethered to the net; and 3) at this instance, either collapsing the container and placing the container into a mailing envelop for delivery to the lab or puncturing/releasing a solution to liberate the analyte of interest from the affinity net, wherein the remaining solution contains the analyte of interest and may be applied to any immunological diagnostic tool or any other analytical method such as Mass Spectrometry or Immunochromatography.

Generally, the collection device improves body fluid diagnostics in the field, at home, in school, in rural settings, or in clinics. In various embodiments, the concentration factor afforded by the collection device may comprise 100×-1,000×, or more, thereby dramatically enhancing the analytical sensitivity of body fluid diagnostic tests; the preservation of the analyte in a solid state out of solution obviates the need for freezing or transport of hazardous liquid body fluid, thereby improving the ease of use and cost of body fluid diagnostic tests. A disinfectant chemical, metal salt, natural antibacterial substance, or any moiety that retards infectious pathogen survival, in one embodiment, may be incorporated into the container or the affinity net material so long as it does not interfere with the diagnostic analyte of interest.

Exemplary Embodiments

In one embodiment, the present disclosure describes aspects of a collection kit that collects a large volume of body fluid and then substantially separates the biomarker content of the fluid while discarding the fluid liquid portion of the sample resulting to thereby concentrate the biomarker content while permitting the collection container to be collapsed. The disclosed collection kit further preserves and amplifies the sensitivity of low abundance biomarkers, regardless of where the sample is collected. In one embodiment, the disclosed collection kit does not require technical manipulations such as magnets, centrifugation, filtration, chromatography, or electrical or chemical steps, treatments or manipulations. In the present disclosure, the collection and concentration is achieved by simply dumping the fluid volume out of the container that is then manually folded flat. Traditional sample collection systems can only collect small volumes of the sample of interest, yet fail to additionally concentrate and preserve targeted biomarkers for analytical techniques. The present disclosure relates to a collection kit that collects biological fluid samples, wherein the collection kit comprises a collapsible container that holds a porous affinity capture net to simultaneously reduce the volume of specimen bodily fluid while concentrating and capturing the desired molecules for biologically relevant markers. Use of the disclosed collection kit is straightforward and requires no advanced equipment to allow for untrained individuals to test/analyze their sample or ship their preserved biomarkers to an external lab.

In various embodiments, the disclosed collection kit may facilitate detection of tuberculosis (e.g., *Mycobacterium tuberculosis* antigens, etc.), Chagas disease, tick-borne diseases, pregnancy, communicable/infectious diseases, malaria, human growth hormone, cancer, cardiac markers, etc. In one embodiment, the disclosed collection kit may enable environmental and geological monitoring and analysis.

Referring now to the figures, for the purposes of example and explanation of the present disclosure, reference is made to FIG. 1, which illustrates an exemplary collapsible container/kit 100, according to one embodiment of the present disclosure. In various embodiments, the container 100 comprises a collapsible/foldable vessel 102 and an affinity net 104. Generally, the vessel 102 permits collection of a fluid (e.g., urine, blood, saliva, sweat, water, etc.). Thus, in various embodiments, the vessel 102 may comprise a viewing window 106 so that the individual filling up the vessel 102 may tell when the vessel 102 is getting full. Similarly, not shown in FIG. 1, the vessel 102 may comprise a fill line or other indicator of the appropriate amount of fluid to place in the vessel 102. In various embodiments, the collapsible vessel 102 is constructed from a waterproof material (e.g., wax-coated paper, plastic, metal, etc.) that is folded into the desired container shape (e.g., cone, box, cylinder, pyramid, etc.).

Generally, the affinity net 104 comprises a collapsible, 3-D, open, continuous net of tethered affinity capture moieties, useful for separating analytes from a fluid sample. In various embodiments, the affinity net 104 comprises a fibrous, strand/yarn like nets or scaffold materials as the backbone. For example, plastic polymers, cellulose, animal or insect derived polymers or strand materials, glass wool, etc.

In one embodiment, the affinity net 104 may comprise activated nitrocellulose fibers (NC). For example, a 1M sulfuric acid solution is mixed with potassium nitrate, and cellulose fibers are fully immersed into this solution for 2 hours. The fibers, in one embodiment, are rinsed until the pH of the solution is neutral. These fibers are mixed with Reactive Blue 221 (RB221) dyed Nanoparticles (NPs). Compared to the affinity strand alone, the increased surface area of the NPs/NC affinity matrix yields a better depletion and stronger (10×) elution of the sample.

In another embodiment of the affinity net 104, nylon 66 fibers may be incubated overnight with RB221 NPs. After subsequent washing of excess NPs, the fibers may be incubated in 100 ng/mL and 0 ng/mL solutions of HCG hormone. After 30 minute incubation, the supernatants are tested. The 100 ng/mL supernatant demonstrates visible depletion.

Figure 2A:
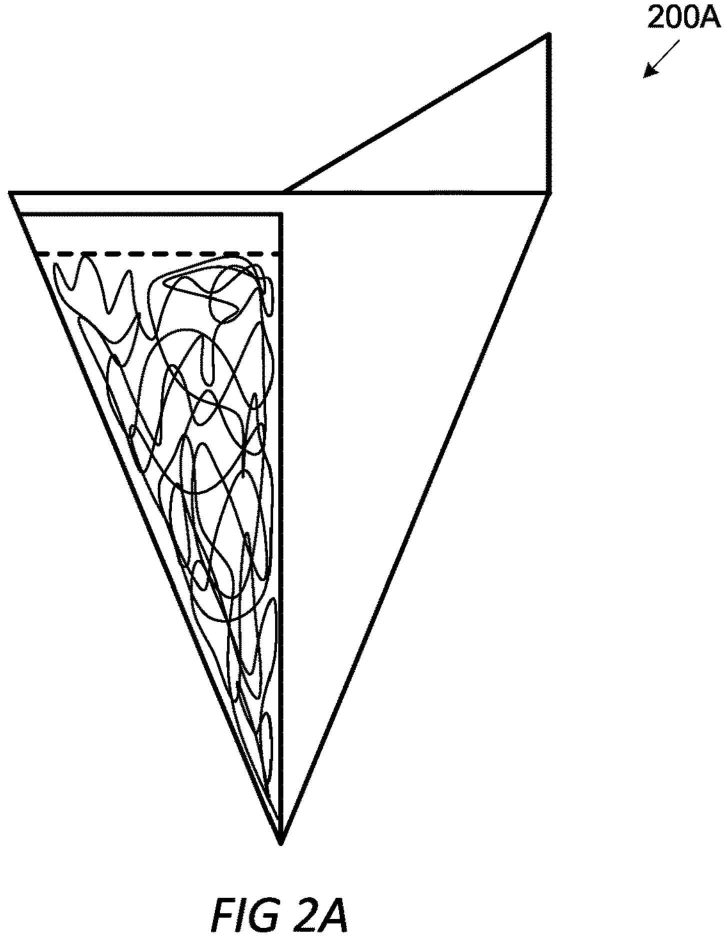
FIG. 2 (consisting of FIGS. 2A and 2B) illustrates an exemplary collapsible container/kit filled with fluid, according to one embodiment of the present disclosure.
Figure 2B:
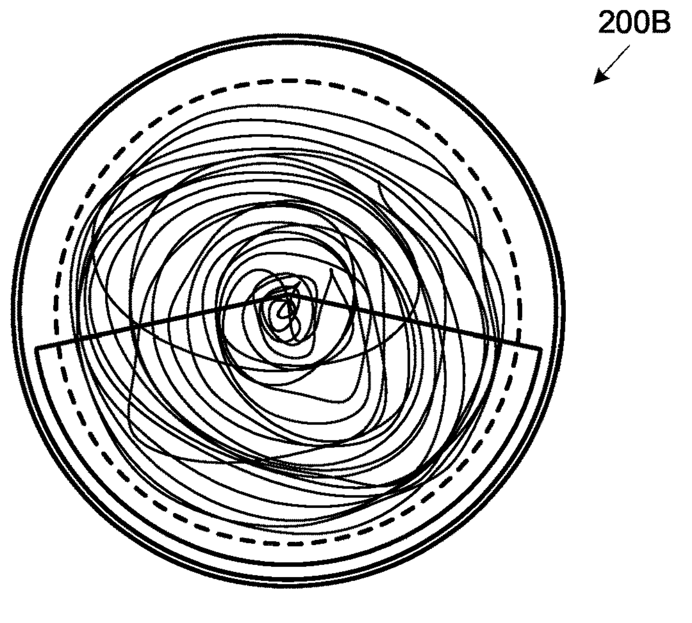

Now referring to FIG. 2 (consisting of FIGS. 2A and 2B), a side view 200A and a top view 200B of an exemplary collapsible container/kit 100 filled with fluid are shown according to one embodiment of the present disclosure. Generally, the fluid is indicated by a dotted line in FIG. 2. In various embodiments, the container 100 is filled until the affinity net 104 is fully submerged in the fluid.

Figures 3, 4:
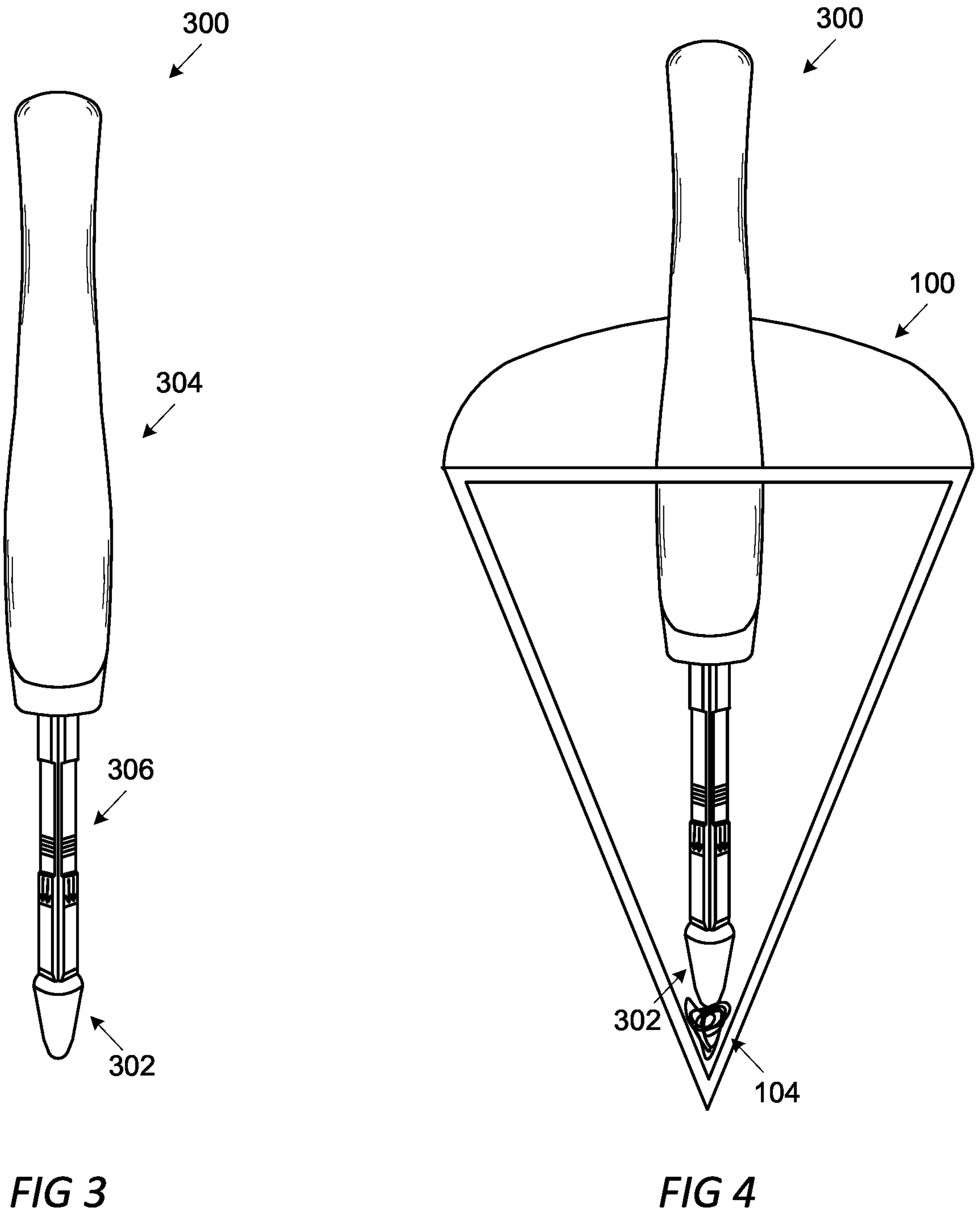
FIG. 3 illustrates an exemplary diagnostic tool, according to one embodiment of the present disclosure.
FIG. 4 illustrates an exemplary diagnostic tool in use with an exemplary collapsible container/kit, according to one embodiment of the present disclosure.

Referring now to FIG. 3, an exemplary diagnostic tool 300 is shown according to one embodiment of the present disclosure. Generally, the tool 300 may be used to analyze specific panel biomarkers in the affinity net 104. In one embodiment, the tool comprises a tip 302 for pushing and compressing the affinity net 104, a handle 304 for gripping the tool 300, and an optional diagnostic strip 306 that permits the measurement of analytes in the affinity net 104. Generally, the diagnostic strip(s) 306 may be designed to measure analytes contained within the affinity net 104 with or without introduction of an elution buffer.

Now referring to FIG. 4, an exemplary diagnostic tool 300 is shown in use with an exemplary collapsible container/kit 100, according to one embodiment of the present disclosure. Generally, the tip 302 may be used to push the affinity net 104 into the bottom of the container 100 such that the analytes contained within it are concentrated for ease of introduction of an elution buffer.

Exemplary Methods of Use

In various embodiments, the disclosed container 100 may be used to collect body fluids (e.g., urine, blood, saliva, vomit, semen, vaginal discharge, fecal matter, mucus, water, alcohol, sweat, etc.) for subsequent analysis. In one non-limiting example: the sample fluid is introduced into the container (e.g., in one embodiment, the subject urinates into the container such that the affinity net 106 is submerged in the sample fluid—indicated by the dotted line in FIG. 2), wherein the analytes of interest are captured by the affinity net. In one embodiment, the affinity net may be allowed to soak in the sample fluid for a predetermined period of time (e.g., 1 second, 5 seconds, 10 seconds, 30 seconds, 1 minute, 2 minutes, 5 minutes, 10 minutes, etc.); then, the sample fluid is removed from the container (e.g., in one embodiment, the subject pours the urine out of the container) and the container is collapsed into a two-dimensional, flat state.

In one embodiment wherein analysis occurs at a different location, the container may then be sealed shut (e.g., using tape, an adhesive strip, etc.), placed in a biohazard bag or other receptacle, and mailed (in another envelope or in the biohazard bag) to a laboratory for further analysis.

In one embodiment, the container is open such that the sample fluid is filtered through the affinity net and flows out of the container, instead of being captured by the container.

Generally, to achieve a substantial removal of the fluid and maximum concentration factor, only the target analyte is preserved within the affinity net that is substantially fluid-free. When an elution buffer is applied, either immediately after collection or at a later point, to the affinity net and the captured analytes generally flow out of the container or dissociate from the affinity net. In various embodiments, the eluted capture material is processed via chemical detection, immunoassay, mass spectrometry, electrical detection system with an electrical output, enzymatic detection system with an electrical output, or magnetic detection system with an electrical output. The analyte is generally preserved by capture or exogenous components. In one embodiment, the analyte is analyzed while still attached to the affinity net.

In one embodiment, the diagnostic tool 300 may be used to compress the affinity net 106 within the container 100 (as shown in FIG. 4) to achieve a higher concentration of target analyte in a smaller volume such that less elution buffer is needed to come into contact with the entirety of the affinity net.

Exemplary Methods of Manufacture

In various embodiments, to manufacture the affinity net 106, a standard weight of glass wool (e.g., 10 g, 20 g, 50 g, 100 g, 200 g, 500 g, 1 kg, 2 kg, 10 kg, etc.) is acid treated (salinization chemicals are sprayed on the fibers) to enable nanoparticle attachment. After the glass wool has dried from acid treatment, in one embodiment, Reactive Blue 221 dyed nanoparticles (e.g., 3 mL, 10 mL, 20 mL, 50 mL, 100 mL, 500 mL, 1,000L, etc.) are incubated with the glass wool for about 1 hour. The dyed glass wool is then, in one embodiment, dried in an oven at about 85° C. for approximately 15 minutes. Washes are generally performed to remove excess nanoparticles. Additionally, the affinity net may be prepared with Toluene to further adhere the nanoparticles onto the glass wool. In one embodiment, the fibers may be cut to a certain length (e.g., 6 inches, 12 inches, 24 inches, etc.)/weight (e.g., 10 g, 20 g, 50 g, 100 g, 200 g, etc.) and freeze dried.

In another particular embodiment to manufacture the affinity net, a standard weight of glass wool will be treated with 3-aminopropyltriethoxysilane and 4,4'-Azobis (4-cyanovaleric acid) will be used to covalently attach amine containing nanoparticles. The nanoparticles will be covalently bound to the glass fibers by reversible cross linkers that are detachable using heat (e.g., approximately 80° C., greater than 50° C., 60° C., 70° C., 80° C., 90° C., 100° C., etc.).

Generally, the container 100 may be manufactured by cutting/scoring a plastic sheet into a predetermined shape. Then, the plastic sheet may be laminated with a plastic sheet. After creasing and folding the plastic sheet into a particular shape, the container may be heat sealed or adhered to complete manufacture of the shape. The present disclosure places no limitations on the types of methods that may be used to manufacture the container 100 (e.g., by hand, by machine, etc.).

To manufacture the collection kit, the nanoparticle incorporated glass wool may be placed inside the waterproof container (e.g., FIG. 1) and instructions for use may be provided therewith. The container is then generally compressed and ready for use.

Exemplary Test Results

A scanning electron microscope analysis of the glass wool with and without nanoparticle incorporation was investigated. Glass without nanoparticles generally display a high surface area available for exposure to the body fluid and its contained analytes, fibrous material. After nanoparticle incorporation, the nanoparticles generally rest on or linked to the surface glass wool fibers.

In one embodiment, a standard weight of glass wool was placed inside of the sample collection container. Next, in one embodiment, water was added to the container until the maximum capacity was reached, measuring to be 80 mL. The container including the glass wool and water was generally weighed. In various embodiments, the water was then dumped out and the container was compressed until all excess water was removed; then, in one embodiment, the container holding just the glass wool now was weighed. Finally, the difference between the two measurements was generally calculated. This experiment protocol was repeated five consecutive times, with results generally shown in Table 1. The average calculated weight was approximately 79.45 grams with a standard deviation of approximately 2.6, which demonstrates an increase in the concentration factor of at least 48% (e.g., Table 1).

TABLE 1

Exemplary test results, according to one embodiment of the present disclosure. The weight (in grams) of the sample collection container, glass wool, and water were collected and recorded. Subsequently, the container and glass wool were weighed after compression of the container and the removal of water.

| | Cone + Wool + 50 mL Water | Cone + Wool (after compression) | Difference | MEAN | ST DEV |
|---|---|---|---|---|---|
| Trial 1 | 55.9052 | 10.3552 | 45.55 | 48.27502 | 1.484246551 |
| Trial 2 | 58.6648 | 10.4732 | 48.1916 | | |
| Trial 3 | 59.4237 | 10.9697 | 48.454 | | |
| Trial 4 | 60.2041 | 10.8302 | 49.3739 | | |
| Trial 5 | 60.4881 | 10.6825 | 49.8056 | | |

An exemplary silver stain analysis of the limit of detection of multiple embodiment of the affinity net was performed using known amounts of the OspA protein for Lyme Disease. Generally, the silver stain analysis was performed using Remazol-dyed nanoparticles tethered to the glass wool. The nanoparticle incorporated glass wool of the affinity net, in one embodiment, successfully depleted a solution contained 2 ng/mL of OspA protein.

A western blot analysis was generally performed using Reactive Blue-dyed nanoparticles tethered to the glass wool. The nanoparticle incorporated glass wool, in one embodiment, successfully depleted a solution contained 0.25 ng/ml of ESAT-6 in phosphate-buffered saline and human urine. The eluates show signal while the supernatants do not, generally demonstrating depletion and capturing by the affinity net.

A dot blot analysis was performed using Reactive Black-dyed nanoparticles tethered to the glass wool. The nanoparticle incorporated glass wool, in one embodiment, successfully captured and amplified urine samples ranging in concentration of 100 pg/mL to 1.23 pg/mL. The affinity net's ability to be consistently reproduced, in one embodiment, was validated by the total depletion of the spike in solution in urine over three different batches.

Analysis of the tethered affinity net's ability to be used for mass spectrometry analysis was performed in one embodiment. ESAT-6 protein and HCG, a marker for pregnancy, was spiked into a urine sample and incubated with the nanoparticle tethered affinity net. In one embodiment, mass spectrometric analysis of these samples produced good spectra and at minimum 2 identified peptide sequences for each protein.

The present disclosure utilizes a unique capture net with tethered affinity molecules placed on their surface. Scanning electron microscope analysis has generally proven that a sample of glass wool treated with acid, dyed hydrogel nanoparticles can be attached. In various embodiments, the affinity net may successfully trap low abundance biomarkers that could not be detected before. In other embodiments, the affinity net can successfully harvest biomarkers and be analyzed for peptide sequences using mass spectrometry.

The affinity net may be coupled with a unique collapsible container to form a collection kit/device. In various embodiments, the disclosed device may be used as follows: 1) the patient opens the collapsible container with the affinity net inside; 2) a bodily fluid sample is then dispersed onto the affinity net; 3) after incubation with the affinity net, the patient then pours out excess bodily fluid; and 4) the patient then collapses the container for shipment to a laboratory. Additionally, an elution buffer may be coupled to the collapsible container, wherein in one embodiment, said user can puncture to release the buffer. After the buffer has been released, the remaining solution will generally contain the analyte of interest which can be applied to any immunological diagnostic tool.

The aforementioned embodiment was screened against 90 users being treated for an active tuberculosis infection in Nepal. Approximately, 88% of the patients preferred the urine collection device as a method for diagnosis compared to standard sputum collection. This demonstrates that this embodiment has been successfully field-tested and user approved.

The aforementioned embodiment has been successfully validated with silver stain analysis and mass spectrometry methods. In several embodiments, the affinity net concentration/elution step has achieved a limit of detection of less than 2 picogram/mL, depending on the initial volume of the sample and the concentration factor as determined by degree of compression of the affinity net into a small volume. The enhanced sensitivity generally may be attributed to the unique double concentration factor achieved by the affinity properties of the hydrogel nanoparticles and the volume reduction of the collapsible container. Additionally, in one embodiment, the collection device may collect low abundance biomarkers for protein discovery in human sweat. In various embodiments, this method of collection has produced many unique proteins, allowing this technology to be used as a powerful non-invasive pre-processing diagnostic tool.

ALTERNATE EMBODIMENTS

In various embodiments, a collection device may be a variety of shapes (e.g., cube, cone, cylinder, tube, envelope, etc.). In one embodiment, the shape of the collection device may be dependent upon the type of fluid to be collected. For example, a collection device may be shaped like a collapsible box, not shown in FIGS. 1-4. After the triangular tabs at the top are pulled, the vessel generally opens into a 3-D state. The tethered affinity net, in various embodiments, may be located within the vessel. The function of this embodiment generally follows the same procedure disclosed herein. Volumetric analyses were performed for this collection vessel (e.g., Table 2).

TABLE 2

Exemplary test results, according to one embodiment of the present disclosure.

| Trials | Filled with Water (g) | Compressed & Empty (g) | Weight Difference (g) |
|---|---|---|---|
| 1 | 80.1357 | 2.5947 | 77.541 |
| 2 | 84.1928 | 2.7404 | 81.4524 |
| 3 | 85.9724 | 2.4017 | 83.5707 |
| 4 | 79.1222 | 2.1779 | 76.9443 |
| 5 | 79.7024 | 1.9603 | 77.7421 |

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. A collapsible container assembly, comprising:

a vessel comprising a nonabsorbent material that is configured to collapse or fold from a first shape into a second shape, wherein:

in the first shape, the vessel defines an opening for accepting a fluid; and the second shape is different from the first shape; and an affinity net that rests within the vessel, wherein the affinity net is comprised of a non-bibulous material and is configured to bind with analytes from the fluid, wherein the affinity net comprises a volumetric body with a plurality of internal open spaces, and wherein the non-bibulous material of the affinity net is configured to be compacted to enable concentration of the analytes captured in the non-bibulous material of the affinity net.

2. The container assembly of claim 1, wherein the vessel further defines a second opening such that the fluid flows through the vessel, coming into contact with the affinity net therein, and out the second opening.

3. The container assembly of claim 1, wherein the nonabsorbent material comprises a plastic, laminated plastic, laminated paper, or laminated cardboard.

4. The container assembly of claim 1, further comprising a viewing window and a fill indicator.

5. The container assembly of claim 1, wherein the affinity net comprises an affinity moiety configured to capture a particular analyte.

6. The container assembly of claim 5, wherein the affinity moiety comprises a dye, ligand, nucleic acid, protein, antibody, aptamer, enzyme substrate, metal, drug, or affinity tag recognizing material.

7. The container assembly of claim 5, wherein the particular analyte is indicative of tuberculosis, Chagas disease, tick-borne diseases, pregnancy, communicable/infectious diseases, malaria, human growth hormone, cancer, or cardiac disease.

8. The container assembly of claim 1, wherein the second shape comprises a flat shape.

9. The container assembly of claim 1, wherein the second shape results in closure of the opening for accepting the fluid.

10. The container assembly of claim 1, wherein the affinity net rests within the vessel in the second shape and the first shape.

11. The container assembly of claim 1, wherein the vessel comprises one or more creases configured to facilitate the collapse or fold of the nonabsorbent material from the first shape to the second shape.

12. The container assembly of claim 1, wherein the affinity net comprises an affinity moiety shielded with an open porous material.

13. The container assembly of claim 1, wherein the affinity net is configured to pull the analytes out of a solution phase.

14. The container assembly of claim 1, wherein the affinity net comprises spun glass silica polymer strands studded with an affinity molecule comprising hydrogel particles and affinity dye molecules.

15. The container assembly of claim 1, further comprising a compacting device configured to compact the affinity net.

16. A collapsible container assembly, comprising:

a vessel comprising a nonabsorbent material that is configured to collapse or fold from a first shape having a first empty volume into a second shape having a second empty volume, wherein:

in the first shape, the vessel defines an opening for accepting a fluid;

the second empty volume is less than the first empty volume; and the second shape is different from the first shape; and an affinity net that rests within the vessel, wherein the affinity net is comprised of a non-bibulous material and is configured to bind with analytes from the fluid, wherein the affinity net comprises a volumetric body with a plurality of internal open spaces, and wherein the non-bibulous material of the affinity net is configured to be compacted to enable concentration of the analytes captured in the non-bibulous material of the affinity net.

17. The container assembly of claim 16, wherein an original volume of the fluid reduces into a second volume and the second volume is 25% or less of the original volume.

18. The container assembly of claim 16, wherein the affinity net fills the first empty volume of the vessel.

19. The container assembly of claim 1, wherein the affinity net is configured to be compacted after accepting the fluid.

20. The container assembly of claim 1, wherein compacting the non-bibulous material of the affinity net is configured to cause a reduction of a volume of the plurality of internal open spaces, and the reduction of the volume of the plurality of internal open spaces is configured to enable the concentration of the analytes.

* * * * *